United States Patent [19]
Miyazaki et al.

[11] 4,434,658
[45] Mar. 6, 1984

[54] ULTRASONIC WAVE TOMOGRAPHIC IMAGING SYSTEM

[75] Inventors: Junji Miyazaki, Yokohama; Hirohide Miwa, Kawasaki; Takaki Shimura, Machida, all of Japan

[73] Assignee: Fujitsu Limited, Kawasaki, Japan

[21] Appl. No.: 253,936

[22] PCT Filed: Jul. 21, 1980

[86] PCT No.: PCT/JP80/00164
§ 371 Date: Mar. 25, 1981
§ 102(e) Date: Mar. 11, 1981

[87] PCT Pub. No.: WO81/00198
PCT Pub. Date: Feb. 5, 1981

[30] Foreign Application Priority Data
Jul. 25, 1979 [JP] Japan .................. 54-94532

[51] Int. Cl.³ .................................. G01N 29/04
[52] U.S. Cl. ........................... 73/618; 73/619; 73/626
[58] Field of Search ............. 73/618, 619, 631, 626

[56] References Cited

U.S. PATENT DOCUMENTS

| | | | |
|---|---|---|---|
| 3,937,066 | 2/1976 | Green et al. .................. | 73/607 |
| 3,979,711 | 9/1976 | Maginness et al. ........... | 73/626 |
| 4,180,790 | 12/1979 | Thomas ...................... | 73/626 |
| 4,253,338 | 3/1981 | Iinuma et al. ................ | 73/626 |

FOREIGN PATENT DOCUMENTS
2607108 10/1976 Fed. Rep. of Germany.

Primary Examiner—Anthony V. Ciarlante
Attorney, Agent, or Firm—Staas & Halsey

[57] ABSTRACT

In an ultrasonic wave tomographic imaging system wherein an acoustic image in an object is focused on the ultrasonic wave receiving means by means of an ultrasonic wave lens in order to pick up an image of the desired tomographic plane in the object, the clearness of a tomographic plane image is much improved by a structure wherein the ultrasonic wave is not generated to unwanted regions other than the desired tomographic plane of the object by providing the ultrasonic wave generating means so that scanning occurs only as to the desired tomographic plane of the object, and a gate means is provided so that the ultrasonic wave receiving means can receive an acoustic image corresponding to the scanning in accordance with the scanning of the ultrasonic wave generating means.

10 Claims, 35 Drawing Figures

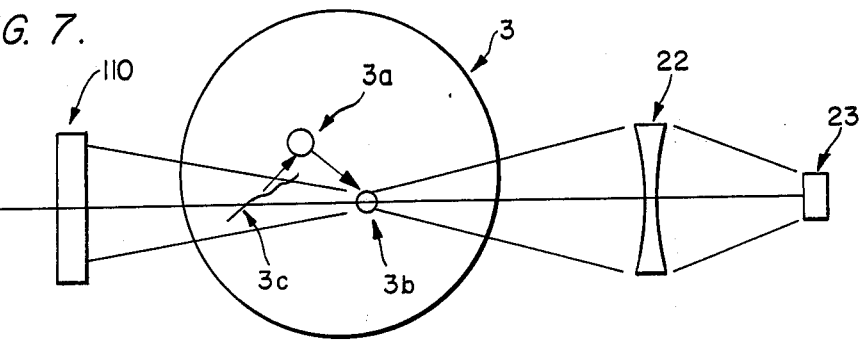
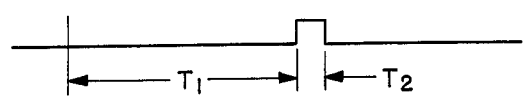
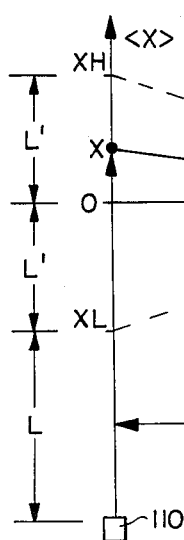
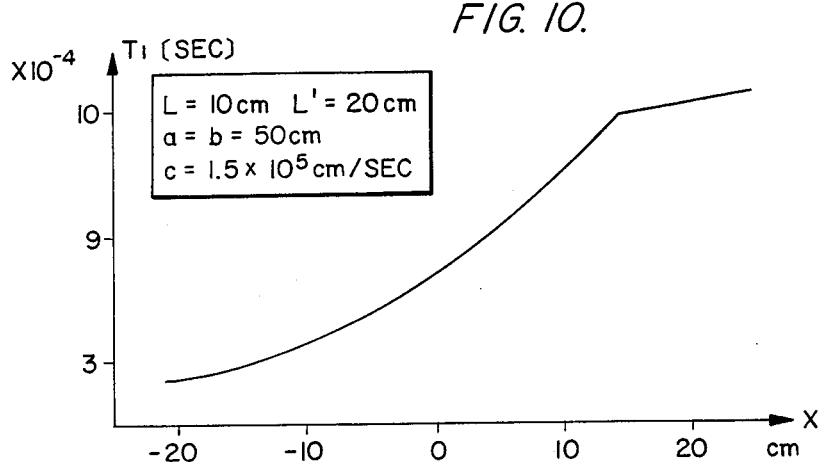

$t_1 > t_2$
$t_{11} - t_1 > t_{21} - t_2$ $t_1 = t_2$
$t_{11} - t_1 = t_{21} - t_2$ $t_1 < t_2$
$t_{11} - t_1 < t_{21} - t_2$

ULTRASONIC WAVE TOMOGRAPHIC IMAGING SYSTEM

BACKGROUND OF THE INVENTION

This invention relates to an ultrasonic wave tomographic imaging system which radiates an ultrasonic wave to an object and reproduces an internal condition of said object as an image from the reflected the wave, the transmitted wave, refracted wave or the scattered wave received from said object, particularly to an ultrasonic wave tomographic imaging system which provides an internal acoustic image having a high S/N ratio.

An ultrasonic wave tomographic imaging system radiates an ultrasonic wave to an object of which the internal condition is to be observed, receives the reflected wave, the transmitted wave or the scattered wave returning from the inside of said object as an internal acoustic image of said object and reproduces an internal condition of said object on the basis of said received waves.

As a system for observing internal condition, an X-ray diagnostic system is widely used. An ultrasonic wave tomographic imaging system, as compared with such an X-ray diagnostic system, is especially not destructive for organs and is less dangerous in the case of a human body as an object. Moreover, it has the merit that it is suited for diagnosis of the soft organs of human body.

As an ultrasonic wave tomographic imaging system, the camera system utilizing an ultrasonic wave lens is already known. This technique is disclosed in the U.S. Pat. No. 3,937,066 "Ultrasonic Camera System and Method".

This ultrasonic camera system has the merits that the desired region can be examined on a real time basis movement of the image can be observed, and the system is superior to the other ultrasonic wave tomographic imaging systems (such as the pulse echo system).

As indicated in FIG. 1, this prior ultrasonic wave tomographic imaging system using a camera is composed of the ultrasonic wave generating means (a generator 1) and the ultrasonic wave receiving means (a receiver 2) which are respectively provided on the opposite side of the object 3.

The generator 1 comprises the ultrasonic wave generator 12 consisting of an electric-acoustic transducer such as a crystal, etc. housed in the case 11, and the contact surface 13 of the case 11 to the object is composed of a flexible organic film having an acoustic impedance which is almost equal to that of the object.

The receiver 2 comprises an ultrasonic wave lens 22 which functions as the ultrasonic wave optical system and an acoustic transducer 23 housed in the case 21, and the contact surface 24 of the case 21 is also composed of an organic film as in the case of said contact surface 13.

The cases 11 and 21 are filled with a medium (for example, water) which has an acoustic impedance almost equal to that of the object 3 such as a human body 3.

The generator 1 and receiver 2 composed respectively as explained above are provided in contact with the object 3 as indicated in FIG. 1, and the ultrasonic wave generator 12 radiates an ultrasonic wave to the object 3.

An acoustic image of object 3 by an ultrasonic wave is focused on the acoustic transducer 23 by means of the ultrasonic wave lens 22.

The ultrasonic wave lens 22 converges the ultrasonic waves as is well known and focuses an acoustic image at the section X in the location determined by the focal distance of the ultrasonic wave lens 22 and a distance between the ultrasonic wave lens 22 and the acoustic transducer 23 thereon.

As the acoustic transducer 23, an acoustic-visual image converter which utilizes an aluminum suspension liquid or an acoustic-electric transducer based on the piezoelectric effect can be used.

In the case of the ultrasonic wave tomographic imaging system of this type, an ultrasonic image of the imaging plane is correctly focused on the transducer 23 in the ideal case, but actually an ultrasonic wave image of the plane X is reflected, refracted or scattered until it reaches the surface of transducer 23, and moreover these images are superimposed to form an obscured image, or said ultrasonic wave image is degraded due to the following major causes of noise, namely the space noise wherein images of other planes than X plane are superimposed to form an obscured image and the timing noise wherein images are superimposed on the image of the plane X with some delay because of the many reflections, refractions and scatterings before they reach the transducer 23 from the generator 12.

FIG. 2 explains the principle why such space noises are superimposed. The ultrasonic waves that are reflected, refracted or scattered (hereinafter simply referred to as reflected) from the point S on the plane X form an image SA having an obscured space intensity distribution as a result of reflections during the travelling process for focusing at the point S' on the surface Y of transducer 23.

Similarly, the ultrasonic waves reflected from the point $S_3$ on the plane X also form a image SD having the obscured space intensity distribution. In addition, the ultrasonic waves reflected from the point $S_1$ which is nearer to the lens 22 than the plane X are focused to the point $S'_1$ which is further than the surface Y, but form a image SB having the unfocused space intensity distribution at the surface Y.

On the other hand, the ultrasonic waves reflected from the point $S_2$ which is further from the lens 22 than the plane X are focused at the point $S'_2$ which is located before the surface Y and thereby form a image SC having the diverged space intensity distribution at the surface Y. As a result, it is a problem to be solved in the ultrasonic wave tomographic imaging system of this type that mutually focused intensity distributions are superimposed as the space noises of other images and thereby an image is obscured.

FIGS. 3(A) and (B) explain the principle where the timing noises are superimposed. The ultrasonic waves reflected from the point S" on the plane X reach the point S''' on the surface Y within a specified time $\Delta T$. On the other hand, the ultrasonic waves reflected from the point S' on the plane X are also multiply reflected at the reflection surfaces $Z_1$, $Z_2$ and reach the point S''' on the surface Y after a delay of $\Delta T$ via the point S''. It is another problem to be solved in the ultrasonic wave tomographic imaging system of this type that the pictures explained above are superimposed as in the case of FIG. 3 (B), the illustrated intensity distribution image S'A on the time axis and thereby, the ultrasonic waves reflected from the point S' becomes the timing noise, obscuring the image.

SUMMARY OF THE INVENTION

It is an object of this invention to eliminate the space noise or/and timing noise mentioned above and to improve the S/N ratio in an ultrasonic wave tomographic imaging system using a camera system as mentioned above.

It is another object of this invention to improve the S/N ratio with the minimum addition in said ultrasonic wave tomographic imaging system using the camera system.

Moreover, it is a further object of this invention to improve said ultrasonic wave tomographic imaging system using the camera system so that a image plane near to the desired plane can be picked up easily while improving the S/N ratio.

This invention involves an ultrasonic wave tomographic imaging system wherein an acoustic image reflecting from the inside of an object is focused on the ultrasonic wave receiving means by means of an ultrasonic lens and thereby an image of the desired image plane in said object is picked up, wherein there is provided means for generating ultrasonic waves for scanning the desired image plane of said object, and a gate means which allows said ultrasonic wave receiving means to receive an acoustic image corresponding to said scanning in accordance with the scanning of said ulrasonic wave generating means.

Moreover, said ultrasonic wave generating, in an embodiment of this invention, is characterized in that said ultrasonic wave is generated from the direction along said desired image plane.

In addition, said ultrasonic wave generating means, in an other embodiment of this invention, is also commonly used as said ultrasonic wave receiving means.

Namely, in this invention the image plane is regionally radiated by the ultrasonic wave, while the entire part of said image plane is radiated in the prior system.

A regional radiation method may be employed in order that the entire part is at first diagnosed and thereafter the ultrasonic wave is regionally radiated only to the region to be examined carefully, whereby the space noise of other regions can be alleviated, making clear an ultrasonic wave image that is obtained. For example, in the case of diagnosis of the nephrolith, the ultrasonic wave is radiated at first to the entire part in order to obtain the total image and then radiated only to the region of the calculus to be examined. Thereby a minute calculus becomes detectable by limiting the space noises reflected from the other regions such as ribs and diaphragm.

Moreover, this regional radiation is useful for combining an image of the entire part with less noise by selecting several region images of the area to be examined. For this purpose, the tomographic plane is often scanned spot by spot with an ultrasonic wave or scanned with a flat ultrasonic wave beam.

Moreover, this invention structures an ultrasonic wave receiving means in order to receive an ultrasonic wave image only of the regionally radiated area of the tomographic plane. For this purpose, as the ultrasonic wave receiving means, a mechanical or electrical space gate means is used which synchronizes with the sequential radiation where an ultrasonic wave image is received, and an electrical signal of an ultrasonic wave is output only from the focusing image plane corresponding to the regional radiation area, for ultrasonic receiving means having a two-dimensional and flat plate. In the same way, a mechanical space gate means which synchronizes with the sequential radiation is used for a one dimensional ultrasonic wave receiving means.

Moreover, this invention comprises a timing gate means in the ultrasonic wave receiving means in order to eliminate a timing noise in such a way that the timing gate means operate in synchronization with the time when the ultrasonic wave transmitted from the ultrasonic wave radiation means reaches the ultrasonic wave receiving means.

BRIEF DESCRIPTION OF DRAWINGS

FIG. 7 explains the timing noise of the embodiment illustrated in FIG. 6.

FIGS. 8(A) to (D) explain the timing gate technique of the embodiment illustrated in FIG. 6.

FIG. 9 and FIG. 10 explain the gate time of the timing gate technique in FIG. 8.

DETAILED DESCRIPTION OF THE PREFERRED EMBODIMENTS

Figure 4:
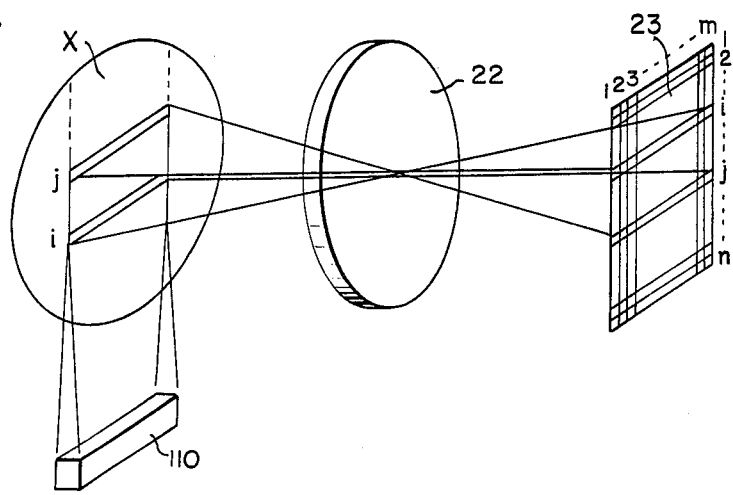
FIG. 4 and FIG. 5 explain the principle of this invention.
Figure 5:
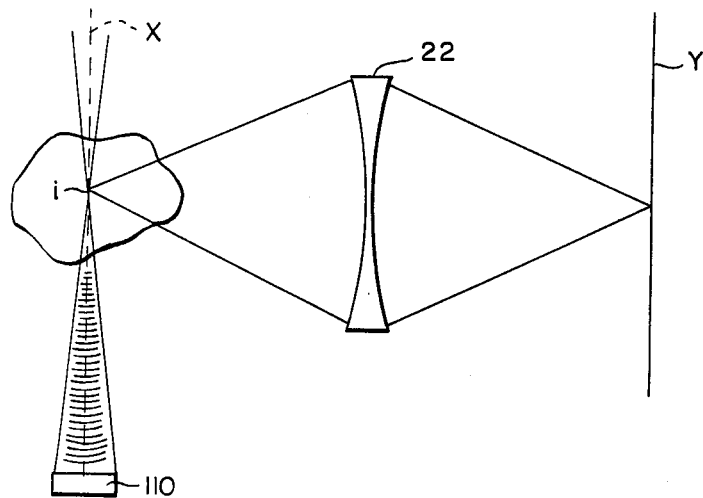

FIG. 4 and FIG. 5 explain the principle of this invention. In these figures, 110 is a generator consisting of at least three rows of piezoelectric conversion elements in a matrix; and it can converge the ultrasonic wave on the straight line i, for example, by giving a phase difference to the drive signals for the central row of the piezoelectric conversion elements from that of the two rows on both sides of the central row. When this phase difference is varied, the straight line of the converged ultrasonic wave moves along the tomographic plane X. For instance, said straight line i moves to j. Namely, an electric focusing method is employed. When this electric focusing method is also employed for the row direction of the piezoelectric conversion element matrix, the spot-by-spot scanning becomes possible.

In case a region having different acoustic impedance exists on the straight line i and j, the focused ultrasonic wave is reflected or scattered and an ultrasonic wave image is transmitted in the vertical direction to the tomographic plane X. The transmitted ultrasonic wave image is converged by the ultrasonic wave lens 22 and focused on the transducer 23 of the image forming surface Y.

This transducer 23 is structured, for example, by piezoelectric conversion element groups arranged in the form at an mxn matrix, and the ultrasonic wave pictures of the straight lines i and j in said plane X are respectively focused on the piezoelectric conversion element groups of the i-th and j-th rows on the transducer 23.

Therefore, a picture corresponding only to the radiated region can be obtained by employing an electric space gate method so that when the ultrasonic wave is radiated to the straight line i, the output of the piezoelectric conversion element groups in the i-th row is extracted at the timing that the ultrasonic wave image reaches the transducer 23, and while the ultrasonic wave is radiated to the straight line j, the output of the piezoelectric conversion element groups in the j-th row is extracted.

In addition, it is also possible to employ a mechanical space gate method where a mask plate having a slit which makes it possible to receive an image only at the i-th row position is used when the ultrasonic wave is radiated to the straight line i, and which is moved in accordance with the sequential radiation to the tomographic plane.

Similarly, a mechanical space gate means can be used, wherein an ultrasonic wave receiving means itself is moved in accordance with the sequential radiation to the tomographic plane, so long as the transducer 23 is the one dimensional ultrasonic wave receiving means. What is more, it is certainly possible to use a mechanical space gate means where the image forming plane is mechanically moved in accordance with a rotating motion of the well known acoustic lens system such as an acoustic prism which is disclosed in U.S. Pat. No. 3,913,061.

When the ulrasonic wave is radiated regionally only to the region to be examined, reflection, scattering and refraction from the areas other than this region are drastically decreased and a clear image having less noise can be obtained.

Figure 6:
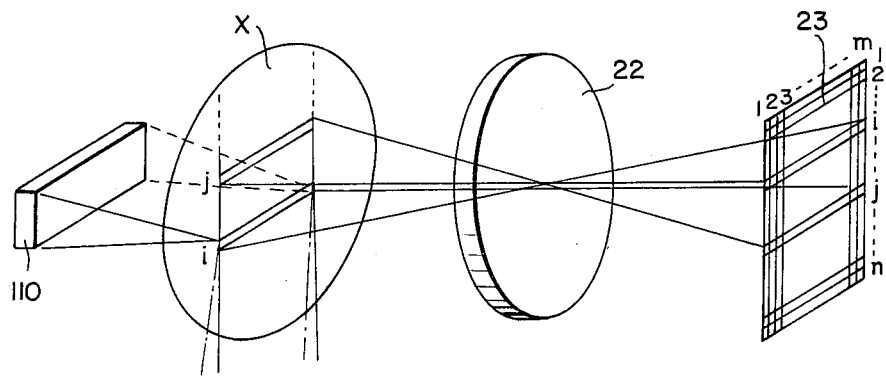
FIG. 6 explains an embodiment of this invention.

FIG. 6 outlines an embodiment of this invention and the difference from that of FIG. 4 is as follows. FIG. 4 shows an example where the ultrasonic wave is radiated from the direction parallel to the tomographic plane X, while FIG. 6 shows an embodiment where the ultrasonic wave is radiated from the direction at a right angle to the tomographic plane X.

The electric timing gate mentioned above is more efficient for noise elimination.

FIG. 7 explains timing noise in the embodiment of FIG. 6. Namely, when the reflecting elements 3a, 3c exist in the generator 110 side of the regionally radiated area 3b of an object 3, the reflected wave of the reflecting element 3c is further reflected by the reflecting element 3a and superimposed to the converged ultrasonic wave sent from the generator 110 at the radiated area 3b. Thus, the superimposed ultrasonic waves are transmitted to the acoustic lens 22. This is a kind of so-called multiple reflections and is a cause of timing noise.

FIGS. 8(A) to (D) explain a transmitting wave and receiving waves. FIG. 8(A) shows a transmitting waveform generated from the generator 110, FIG. 8(B) is a receiving waveform before it is electrically gated by the transducer 23, FIG. 8(C) is a gate signal waveform and FIG. 8(D) gated receiving waveform.

As indicated in FIG. 8(B), the multiply reflected waves reach the regionally radiated area 3b with some delay from the not-reflected radiated wave. In other words, an acoustic output b2 by the multiply reflected wave is received with some delay from an acoustic output b1 by the radiated ultrasonic wave.

Therefore, required is to obtain only an output b1 by giving such a gate signal (FIG. 8 (c)) so as to eliminate acoustic output b2.

The time $T_1$ from generation to gating can be obtained by dividing the transmission distance of the ultrasonic wave with the transmission rate.

FIG. 9 explains a method of obtaining this time $T_1$. The ultrasonic wave generated from the generator 110 is transmitted to the direction $<x>$ along the plane to be examined and is reflected at the position x, and then reaches the position x' on the axis $<x>$ where the transducer exists, having passed the acoustic lens 22.

Let the symbols a, b, L and L' be respectively considered as the relevant distances of each specified cross-section. When the transmission rate of the ultrasonic wave is considered as C, the time $T_1$ for the cross section at the point x (FIG. 9) is expressed by the following equation.

$$T_1 = (L + L' + x + (1 + b/a) \cdot \sqrt{a^2 + b^2})/C$$

In FIG. 9, x'H and x'L respectively indicate the highest and lowest piezoelectric conversion elements of the matrix, and xH and xL indicate respectively the reflected points on the $<x>$ axis of the ultrasonic waves received by the elements of x'H and x'L.

As an embodiment, the radiation method indicated in FIG. 4 is employed. In addition, the above explanation can also be applied to the radiation method of FIG. 6.

The graph of FIG. 10 shows the relation between $T_1$ and x. In this case, parameters are as follows. $a = b = 50$ (cm), $c = 1.5 \times 10^5$ (cm/sec), $L = 10$ (cm), and $L' = 20$ (cm). As indicated in this graph, the time $T_1$ from generation of the ultrasonic wave to the gating is determined definitely in accordance with the position x of the converged area. In addition, the period of the gating $T_2$ is also determined definitely in accordance with the number of waves and their route differences through the acoustic lens.

An electric focusing method for electrically focusing the ultrasonic waves will be explained below in more detail.

Figure 11:
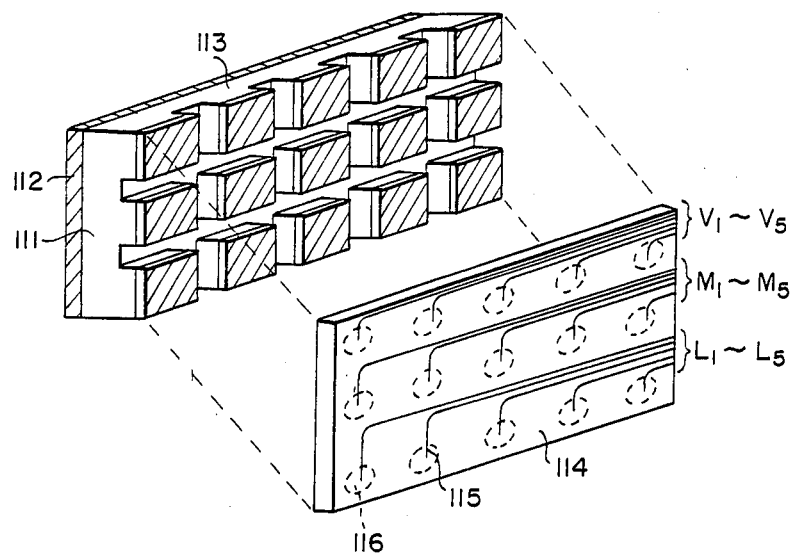
FIG. 11 and FIG. 12 explain electronic focusing techniques used in FIG. 4 and FIG. 6.
Figure 12:
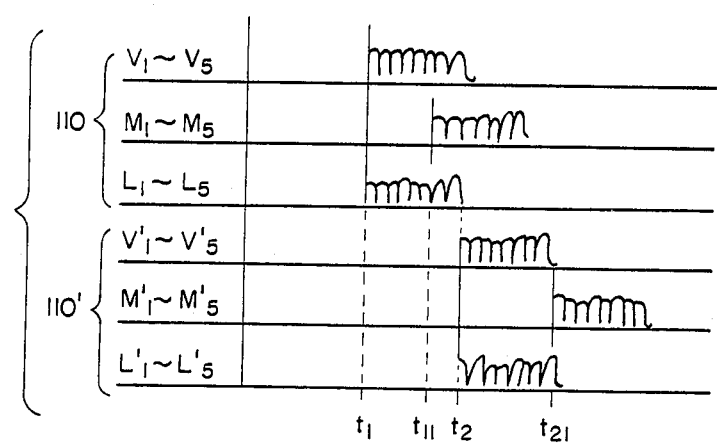

FIG. 11 shows a detailed structure of the generator 110, while FIG. 12 shows the driving waveforms.

The one side of the piezoelectric substrate 111 such as crystal or ceramic etc. is coated with the common electrode 112 and the other side is divided into 15 transducers (5×3), each of which has individual electrodes 113. On the bonding side of the wiring plate 114 which is bonded to individual electrodes, the lead-out electrodes 116 are formed on the positions corresponding to individual electrodes, while on the other side of the wiring plate 114, the wirings $V_1$ to $V_5$, $M_1$ to $M_5$ and $L_1$ to $L_5$ are wired as the printed wirings. Each wiring, in addition, and each leadout electrode are respectively connected via the through holes 115.

When, an in-phase drive signal is applied to the wirings $V_1$ to $V_5$ and $L_1$ to $L_5$, and a delayed drive signal is applied to the wirings $M_1$ to $M_5$ respectively, the ultrasonic wave is transmitted to the common electrode 112 in such a way as to converge to the center from the outer two rows ($V_1$ to $V_5$ and $L_1$ to $L_5$). At this time, the desired row or focusing line L where the ultrasonic wave is focused along a single line is determined by a delay of phase given to the wirings $M_1$ to $M_5$. Therefore, the focusing line L can be moved to the desired position of the tomographic surface X by adjusting said amount of phase delay. Moreover, the straight line L is moved over the desired range on the surface X, the reflected waves from the straight lines L with equal intervals are sampled and each wave is sequentially memorized as the data of a single raster scanning of the display unit. Thereafter, when the stored data is read out and displayed in synchronization with the raster scanning of the display unit, display of the desired range on the plane X can be made with less noise.

In this case, since the ultrasonic wave is attenuated, the received wave becomes weaker as it becomes farther from the generator. Therefore, the receiving sensitivity must be changed automatically in accordance with the distance from the generator along the straight focusing line L.

Figure 13:
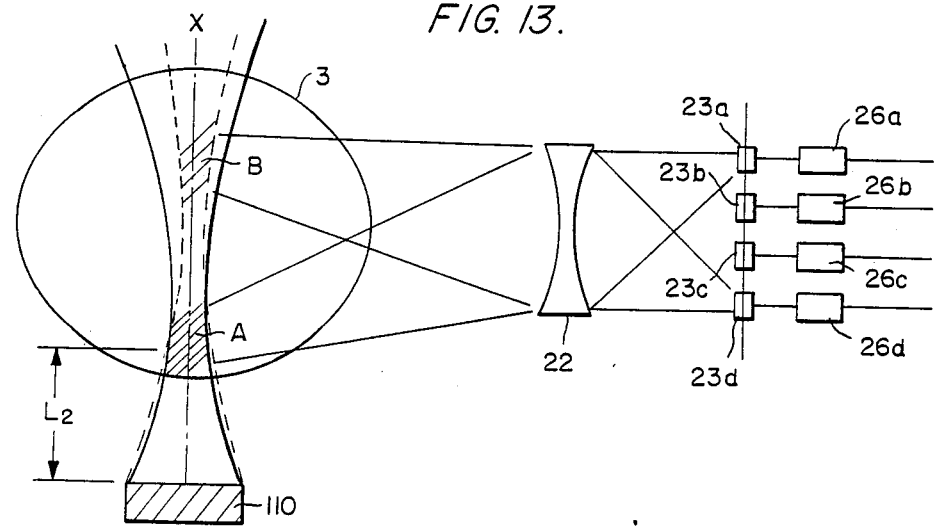
FIG. 13 explains an embodiment of the gain adjusting technique used in the structure indicated in FIG. 4.

FIG. 13 explains receiving sensitivity change-over in the embodiment of this invention. In this figure, 23a to 23d four rows of receiving elements are shown for simplification of explanation of an example of the matrix receiving array. 26a to 26d are amplifiers corresponding to the receiving elements 23a to 23d. When the ultrasonic wave is focused to the point A of focal plane X of the object 3 from the generator 110, its acoustic image is focused to the receiving element 23d by means of the acoustic lens 22. As explained above, since the intensity of the ultrasonic wave is different for the focused points A and B, such difference must be corrected at the receiving side. Namely, a gain of the amplifier 26a is set in accordance with the distance $L_2$ *from the focal point A and the generator* 110. *A gain of the amplifiers* 26b, 26c is similarly set in accordance with the distance between the corresponding focal point and the generator 110. In this embodiment, the gain of the amplifier 26d is minimum, while the gain of the amplifier 26a is maximum. The gain of the amplifiers of each row of the matrix array is set as explained above.

Here, the gain setting is no longer necessary if intensity difference is suppressed by using a non-linear circuit such as a log-amplifier.

Figure 14A:
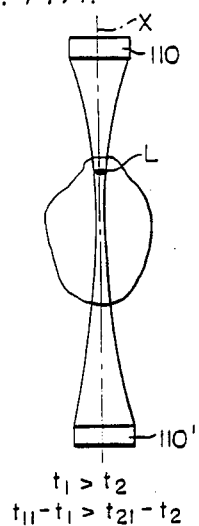
FIGS. 14(A) to (C) explain another embodiment of the gain adjusting technique used in the structure indicated in FIG. 4.
Figure 14B:
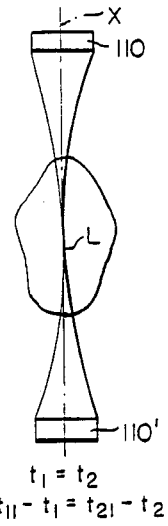
Figure 14C:
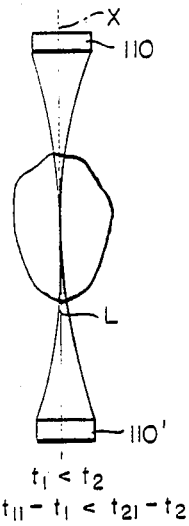

The intensity of the ultrasonic wave becomes independent of the distance from the generator along the straight line L by providing generators in the couple of areas facing each other in the vicinity of the plane X. FIG. 14 shows an example where a couple of opposing generators are used. A couple of generators 110 and 110' like those in FIG. 10 are provided face to face in the vicinity of the plane X.

The focusing line L moves as indicated in FIG. 14 (A) to (C) in accordance with relation of the timings $t_1$, $t_{11}$, $t_2$ and $t_{21}$ in FIG. 12 where the drive signal is applied to each row of vibrators of a pair of generators 110 and 110'. Since a pair of ultrasonic wave generators are located face to face vertically, the sum of the intensity of the ultrasonic waves becomes symmetrical and thereby a difference of intensity due to attenuation can be significantly reduced.

Figure 15:
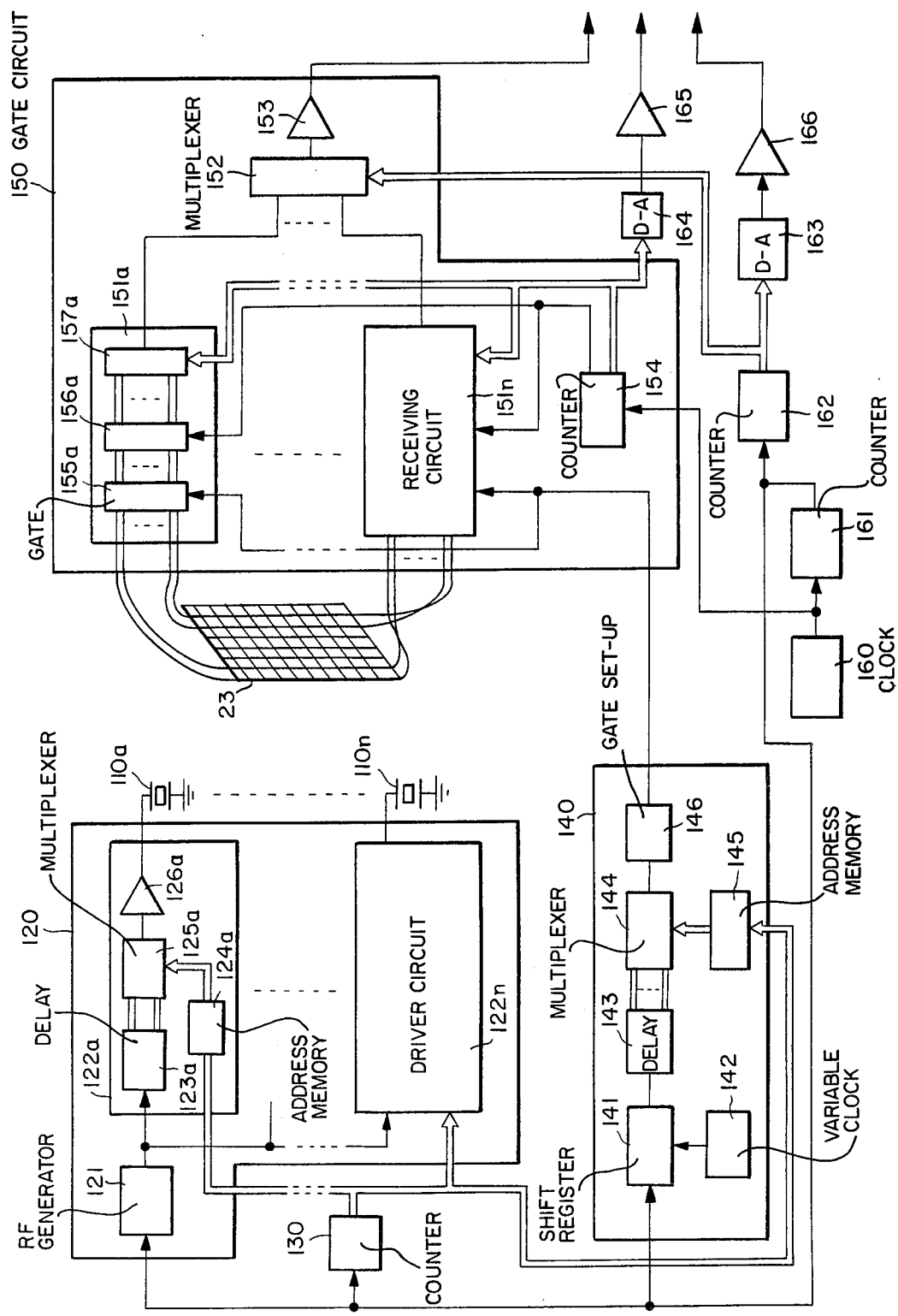
FIG. 15 illustrates the block diagram of an embodiment of this invention.

FIG. 15 illustrates the block diagram of an embodiment of this invention.

In this figure, 120 is the electronic focusing circuit; this circuit drives the piezoelectric conversion elements 110a to 110n of the generator 110, based on the principle of FIG. 11 and FIG. 12, in view of the electronic focusing and scanning. 130 is the scanning position address counter; 140 is the gate signal generator. 150 is the electronic gate circuit, which receives the outputs of the piezoelectronic conversion elements of each row and column of the piezoelectric conversion element array and samples the output of the piezoelectric conversion elements in the specified row with the address signal and the output of gate signal generator 140. 160 is the reference clock oscillator; 161 is the 256-bit counter for generating the horizontal synchronization signal; 162 is the horizontal synchronization signal address counter; 163, 164 are the digital-analog converters; and 165, 166 are the amplifiers.

The electronic focusing circuit 120 is composed of the RF wave generator 121 and drive circuits 122a to 122n for individually driving the piezoelectric conversion element groups 110a to 110n of each row.

When an output of the horizontal synchronization signal counter 161 is input, the RF wave generator 121 generates a burst wave consisting of a plurality of sine waves. Usually, two or three waves are used as the burst wave.

The output of the RF wave generator 121 is input to the drive circuits 122a to 122n.

The drive circuits 122a to 122n comprise the delay circuits 123a to 123n, address memories 124a to 124n, multiplexer circuits 125a to 125n and amplifiers 126a to 126n.

The address memories 124a to 124n are controlled by a count value which is the output of the address counter 130, and the address counter 130 counts the horizontal synchronization signals.

For example, when the number of scanning lines of the display screen is selected to 256, the address counter 130 is a 256-bit counter. Namely, the address counter 130 generates the address from 0 to 255 and this address is the address information of the read-only-memory of the address memories 124a to 124n.

The address memories 124a to 124n store the selection signals of multiplexer circuits 125a to 125n in individual addresses.

Meanwhile, the burst output the RF wave generator 121 is input to the delay circuits 123a to 123n. These delay circuits input in parallel to the multiplexer circuits 125a to 125n the 256 kinds of delayed output having different delay times.

The multiplexer circuits 125a to 125n receive the output of aforementioned address memories 124a to 124n and output the specified delayed output among these delayed outputs.

These delayed outputs are amplified by the amplifiers 126a to 126n and given to the individual piezoelectric conversion elements 110a to 110n. Thus, these elements are driven, generating ultrasonic waves.

Namely, each address of the address memories 124a to 124n must store the selection signal for selecting the delayed output in such a way that the ultrasonic wave is focused on the area corresponding to the address specified by the address counter 130.

The electronic focusing operation is performed as explained above, and thereby the tomographic plane is sequentially scanned.

The gate signal is also generated in synchronization with the electronic focusing operation by means of the horizontal synchronization signal.

Namely, the gate signal generator 140 comprises the shift register 141, variable time clock generator 142, delay circuit 143, multiplexer 144, address memory 145 consisting of a read only memory and the gate width set-up circuit 146 consisting of the one-shot multi-vibrator.

The horizontal synchronization signal is delayed by the shift register and a delay time can be controlled by an output of the variable time clock generator 142. A delay time of the shift register 141 is so adjusted that the minimum time $T_0$ of the ultrasonic wave generated from the generator 110 required from passing a human body 3 until reaching the receiving element 23 via the lens is obtained.

The horizontal synchronization signal delayed by the shift register 141 is fine-adjusted for its delay time by the delay circuit 143. This delay time compensates, in case the number of scanning lines (rows) is selected to 256 for example, for a difference of the minimum times in said scanning operations for every scanning for focusing.

For this reason, the delayed outputs are output in accordance with the scanning lines, for example 256, from the delay circuit 143.

These outputs are input to the multiplexer circuit 144. On the other hand, the address for focusing and scanning is given from the address counter 130. The address register 145 receives the address and outputs a selection signal to the multiplexer circuit 144 in order to select a delayed output which is most suitable for the scanning of the address.

An output of this multiplexer circuit 144 is widened for the time corresponding to the number of RF waves at the gate width set-up circuit 146 and then output as the gate signal.

Meanwhile, the electronic gate circuit 150 is connected to each piezoelectric conversion element of the piezoelectric conversion matrix 23 of n rows and m columns. The m outputs of the m piezoelectric conversion elements of the first row are input to the receiving circuit 151a and then the m outputs of the piezoelectric conversion elements of the other rows are sequentially input to the corresponding receiving circuits with the outputs from the n-th row being input to the receiving circuit 151n.

The receiving circuits 151a to 151n are respectively composed of the gate circuits 155a to 155n, memory circuits 156a to 156n, multiplexer circuits 157a to 157n. A number m of the gate circuits 155a to 155n and memory circuits 156a to 156n are respectively provided for the m columns. But all the m circuits of each row are indicated as one block in the figure.

The m gate units of the gate circuits 155a to 155n are given as inputs said data signals.

The gate circuits 155a to 155n send m receiving inputs by means of the gate signal to the memory circuits 156a to 156n. The m memory units of the memory circuits 156a to 156n respectively store the gate outputs.

On the other hand, the address counter 154 of the electronic gate circuit 150 receives the clocks of the reference clock generator 160, counts them and outputs the counted value. This address counter is designed as an m-bit counter (counts each m clock pulses), covering the number of columns of the piezoelectric conversion element matrix.

This counted value output is input to the multiplexers 157a to 157n and therefore the parallel outputs of the multiplexers 157a to 157n are converted to serial outputs. The memory circuits 156a to 156n are reset by the count-up signal from the address counter 154 for the next receiving input.

These n serial outputs are input in parallel to the multiplexer 152. On the other hand, the multiplexer 152 receives a counted value of the address counter 162 which counts the horizontal synchronization signals.

Therefore, the multiplexer 152 outputs only one serial input corresponding to a counted value of the address counter 162 among n serial inputs. The address counter 162 is designed as an n-bit counter (counts every n pulses), covering the n rows of the matrix. Therefore, when the number of scanning lines is selected to be 256, n is selected to be 256.

An output of this multiplexer 152 is amplified by the amplifier 153 and is used by the display unit as the luminance signal.

Meanwhile, an output of the address counter 162 is converted to an analog signal by the digital-analog converter 163, amplified by the amplifier 166 and used as the vertical (Y-axis) deflection signal for the display unit. Similarly, an output of the address counter 154 is also converted to an analog signal by the digital-analog converter 164, amplified by the amplifier 165 and used as the horizontal (X-axis) deflection signal for the display unit.

The abovementioned operations are summarized below. The drive circuits 122a to 122n are controlled so that the ultrasonic waves are focused and scanned to the scanning position of the plane specified by the address counter 130, the gate signal which is delayed in accordance with the scanning position specified is generated by the gate signal generator 140, each receiving input of the m×n piezoelectric conversion element matrix 23 is sampled by this gate signal, the sampled signal is converted to the serial signal, and thereafter the serial signal corresponding to the row of the receiving position corresponding to said scanning position specified by the address counter 162 is output by the multiplexer circuit 152.

In addition to the foregoing description, this invention includes the generator and receiver operating with the same unit.

Namely, in this invention, the ultrasonic wave generated from the piezoelectric converter is deflected and focused by the acoustic lens system and an acoustic deflection system and then radiated to the region of an object to be examined. Thereafter, the ultrasonic wave reflected from such region is in turn deflected and focused again by the acoustic lens system and the acoustic deflection system and then received by the piezoelectric converter.

Figure 16:
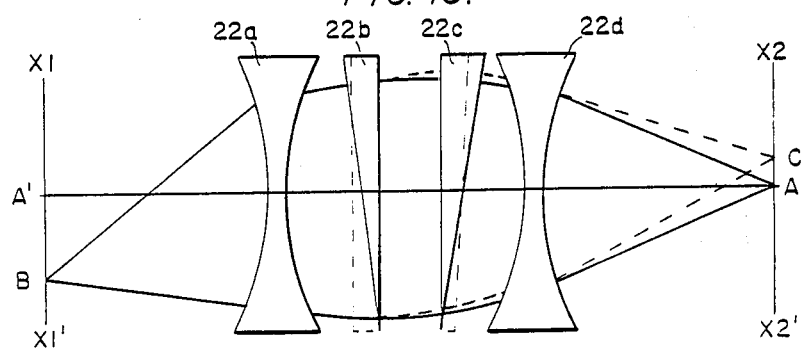
FIG. 16 explains another embodiment of this invention.

FIG. 16 illustrates a structure of the second embodiment of this invention. In this figure, 22a and 22d are acoustic lenses; 22b and 22c are comb-shaped prisms; $X_1$, $X_1'$ is an internal cross-section of an object and $X_2$, $X_2'$ is a picture forming surface.

In the same figure, a piezoelectric converter is provided vertically to the paper surface at the position A and then a pair of comb-shaped prisms 22b and 22c are be adjusted so that an acoustic image moves reciprocally in the vertical direction $X_1$, $X_1'$ about the point A'. When the ultrasonic pulses are sequentially generated from the point A, these pulses are focused and deflected by the lenses 22a and 22d and the prisms 22b and 22c, and then sequentially radiated to each point of the cross-section $X_1$, $X_1'$. In the case when all the piezoelectric elements send and subsequently receive a pulse together, and adjustment is made so that each piezoelectric element sends and receives the pulses for a number of times equal to the number of scanning lines of the display unit while the prism rotates 180 degrees, so that one full picture can be obtained when the prism makes a half turn.

In this embodiment, the ultrasonic wave is regionally radiated to the cross-section $X_1$, $X_1'$ of an object, and therefore a strong reflected wave, resulting in, a clear image can be obtained with less noise due to reflections from the other regions. In addition, a piezoelectric converter (transducer) is commonly used for transmission and reception of the ultrasonic wave, thus simplifying the structure of the system.

If the ultrasonic wave transmitted from the point A is focused on the point B, the reflected wave does not return to the point A but to the other point a little shifted from the point A, the point C, for example, because a prism already makes a little turn when the reflected wave from the point B passes through the prism. Therefore, it is required to use a piezoelectric converter having a sufficient width for covering such a shift of the focusing position. Here, the transmission rate of the ultrasonic wave and the rotation speed of the prism are respectively considered as constant and the shift of the focusing position explained above depends on the distance from the prism to the cross-section of the object and the distance from the prism to the picture forming surface. The aforementioned distances mutually have the following relation, namely when the one becomes shorter, the other becomes longer. Therefore, the shift becomes almost constant when the region to be examined is deeper or shallower.

This shift can be ignored when a piezoelectric converter is sufficiently wide, but a wider transducer may pick up noise. Therefore, it is desirable considering the problem mentioned above to provide a control means so that the reflected wave from the cross-section of an object is selectively received only at the focusing position on the piezoelectric converter. As the above control means, the following three methods can be employed.

In the first method, as indicated in FIG. 17 (A), a plurality of conversion units 23a to 23b (7 units in this case) arranged in parallel are used as the piezoelectric converter 23 and a conversion unit located in the focusing area is selected electrically in accordance with the shift of the focusing position. Also, the conversion unit as indicated in FIG. 17 (B) can be used, where the common electrode 311 is provided on one side of a long and slender piezoelectric plate 310, with the individual electrodes 312 on the projected areas of the other side. Moreover as the electrical selection means, a selection circuit 50 which sequentially selects the conversion units of the transducer 23 is provided as indicated in FIG. 17 (C), and thereby a conversion unit is selected for reception in accordance with the rotating angle information sent from the prism rotating angle detector 40. The received signal is sent to the signal processing circuit 60 and converted to a picture signal therein and displayed on the CRT. Since the shift of the focusing points due to the prism changes according to the sine function of the time, selection by the selection circuit 50 should be made at the timing which changes according to the sine function. In this case, it is also possible to transmit the ultrasonic wave from the conversion unit 23a and receive it with the conversion units 23a and 23b, or to transmit from the units 23a and 23b, and receive with the unit 23a. When selective reception is realized by a narrow single conversion unit, an incoming noise can be suppressed outstandingly as compared with the reception with a single piezoelectric converter having a width as wide as seven conversion units.

Figure 18A:
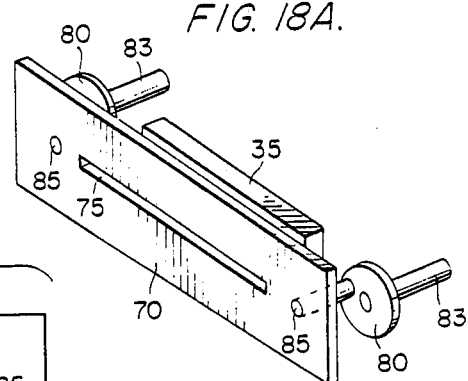
FIGS. 18(A) and (B) explain the second embodiment of the selective reception technique used in the embodiment of FIG. 16.
Figure 18B:
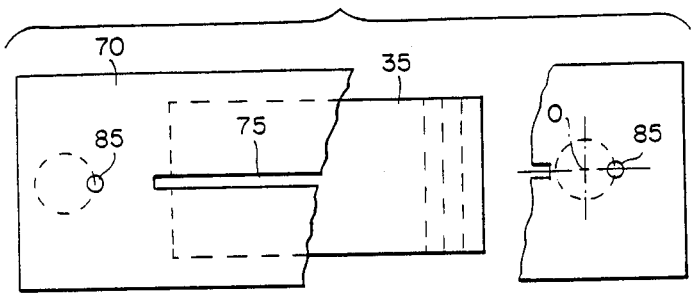

The second method of the control means is indicated in FIGS. 18(A) and (B), where a slit mechanism is employed. As the piezoelectric converter, a wider conversion unit 35 is used, a mask plate 70 having a slit 75 is provided in front of said conversion unit, and this mask plate moves in conjunction with the rotating disk 80 by means of the pin 85. The rotating disk 80 rotates in synchronization with a rotation of the prism via the rotating axis 83 of an electric motor. Therefore, the slit 75 makes a reciprocal motion vertically according to the sine function. Each element (shown by the dotted lines) of the conversion unit transmits and receives the ultrasonic wave but selective reception can be done at the area corresponding to the slit.

The third method of control means is as follow. The focusing point is shifted reciprocally at a constant speed by controlling the rotating speed of a prism and a conversion unit is selected at the same timing by using the piezoelectric converters and the selection circuit means as in the case of the first method.

Accordingly, a method for controlling the rotating speed of the prism is now explained. When a prism rotates at a constant speed, the shift of the focusing point y on the picture forming surface $X_2$, $X_2'$ can be expressed by the following equation $$y = A_0 \cdot \sin(W_0 t) \tag{1}$$

where t is time, $W_0$ is the constant angular speed of the prism and $A_0$ is an amplitude. If the rotating speed of the prism is considered to be a function W(t) of time to cause the shift of the focusing point to change linearly, and if the rotated angle is defined as $$\theta(t) = \int W(t)dt,$$

then it follows that $$y = B_0 \cdot \sin \theta(t) = Kt \tag{2}$$

where K is a proportional constant and $B_0$ is an amplitude, for $\theta(t)$ within the range $$0 \leq \theta(t) \leq \pi/2$$

From equation (2), $$\theta(t) = \sin^{-1} Kt/B_0 \tag{3}$$

When the equation (3) is differentiated, the angular speed of the prism as a function of time is:

$$W(t) = d\theta(t)/dt = 1/[(B_0/K)^2 - t^2]^{\frac{1}{2}} \quad (4)$$

Therefore, when $t = B_0/K$, $W(B_0/K)$ from equation (4) is infinite and $\theta(B_0/K)$ from equation (3) is $\pi/2$. Since it is impossible to make an angular speed infinite, it is also impossible to linearly control the shift of the focusing point y up to the value of $\pi/2$ for the rotation angle. Accordingly the value of $B_0$ is set to be larger than $A_0$, and y of equation (2) is considered to change at constant speed until it equals $A_0$, and thereafter a different control is provided.

Various kinds of other control methods are possible, for instance, if rotation is continued with the angular speed being the same as when y becomes $A_0$. At this time, the angular speed is given by the following equation $$[W(t)]_{(t=A_0/K)} = [d\theta(t)/dt]_{(t=A_0/K)} = (K/A_0)/(n^2-1)^{\frac{1}{2}} \quad (5)$$

$$\text{for } B_0 = n \cdot A_0 \text{ and } n > 1. \quad (6)$$

The prism rotates through an angle corresponding to $y = A_0$ during the time up to $t = A_0/K$. Accordingly, from equations (3) and (6), $$\theta(A_0/K) = \sin^{-1}(1/n) \quad (7)$$

Therefore, the angle for which rotation should be made at a constant speed within the first quadrant may be expressed as $$\pi/2 - \theta(A_0/K) = \pi/2 - \sin^{-1}(1/n) \quad (8)$$

If the time for a rotating angle $\theta(t)$ to change from 0 to $\pi/2$ is to be equal to the time $\pi/(2W_0)$ for a similar rotation at the constant speed $W_0$, since equation (8) is equal to equation (5) multiplied by $[\pi/(2W_0) - A_0/K]$, the following relation is obtained:

$$[\pi/(2W_0) - A_0/K] \cdot (K/A_0)/(n^2-1)^{\frac{1}{2}} = \pi/2 - \sin^{-1}(1/n), \text{ so that}$$
$$K = (2W_0/\pi) \cdot A_0[(n^2-1)^{\frac{1}{2}}(\pi/2 - \sin^{-1}(1/n)) + 1] \quad (9)$$

Equation (9) yields, for $n = 2$, $$K = (2W_0/\pi) \cdot A_0 \cdot (\pi/3 + 1) \quad (10)$$

The following equation is obtained from substituting equation (10) into equation (4), $$B_0/K = 2A_0/K = \pi/[W_0(\pi/3+1)], \text{ so that}$$
$$W(t) = [(\pi/W_0(\pi/3+1))^2 - t^2]^{-\frac{1}{2}} \quad (11)$$

for the range $0 \leq t \leq A_0/K$.

In other areas, the rotation speed should be constant up to the time $t = B_0/K$. Analysis can be done in the same manner for times after $t = B_0/K$. Namely, only the rotation control as expressed by equation (11) is required.

Figure 19:
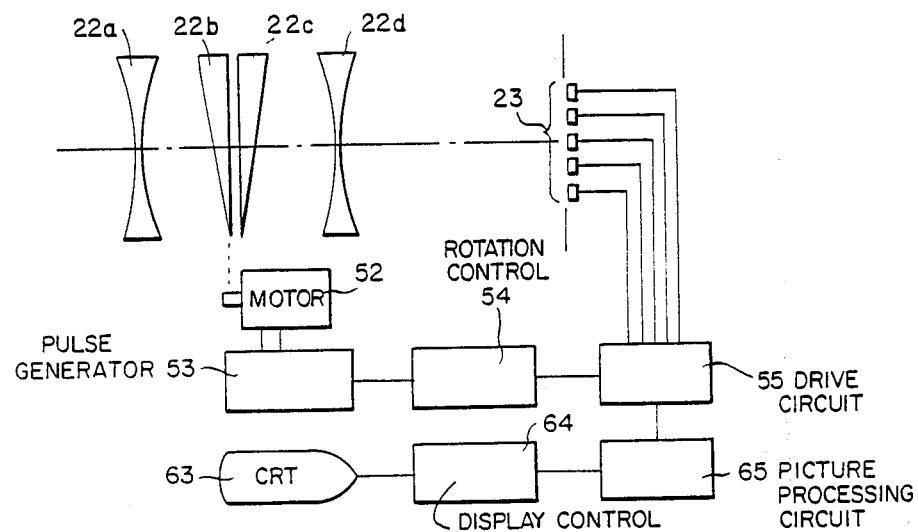
FIG. 19 explains the third embodiment of the selective reception technique used in the embodiment of FIG. 16.

FIG. 19 shows an embodiment of a circuit structure for setting forth the 3rd method of the control means. The abovementioned rotating angle $\theta(t)$ or $W(t)$ is programmed for time in the rotation control circuit 54, and the pulse motor drive circuit 53 drives a pulse motor 52 in accordance with such a programmed signal, causing the prisms 22b and 22c to rotate at the programmed rotating speed. During this time, a programmed prism rotating angle data is sent to the selective drive circuit 55 from the rotation control circuit 54, and thereby a conversion unit is selected for transmission and reception of the ultrasonic wave. The received signal is converted to a picture signal in the signal processing circuit 65 and displayed on the CRT 63 through the display control circuit 64. Moreover, this invention is capable of obtaining an acoustic image of a different tomographic plane by making use of the regional radiation method.

Namely, the ultrasonic wave is regionally radiated to a tomographic plane, an acoustic energy which is almost the same as that radiated to the region to be examined is radiated, in case the focal depth of the lens is deep, to the regions in the generator side or in the opposite side in the vicinity of said region to be examined, and therefore a time difference occurs in the receiving timings of the waves reflected from the respective regions. This invention has succeeded in freely changing the receiving timings using such time difference, and thereby displays clearly the images of the tomographic plane near to that including the region to be examined. Therefore, in the present invention, the ultrasonic wave receiving means is so structured that only the ultrasonic wave image of the regionally radiated area of the tomographic plane can be received. For this purpose, as the ultrasonic wave receiving means, a functional or electrical space gate means which synchronizes with such sequential radiation, so that only the area on the image forming surface corresponding to the regionally radiated area receives an ultrasonic picture or outputs an electrical signal of such ultrasonic image, is provided for the two-dimensional and flat ultrasonic wave receiving means. In the same way, a mechanical space gate means which synchronizes with the sequential radiation may be for a single dimensional ultrasonic wave receiving means.

Moreover, in this invention, the ultrasonic wave receiving means includes the timing gate means and space noises are eliminated by the timing gate means which is designed for operating in synchronization with the time required by the ultrasonic wave to reach the ultrasonic wave receiving means from the generator.

Figure 1:
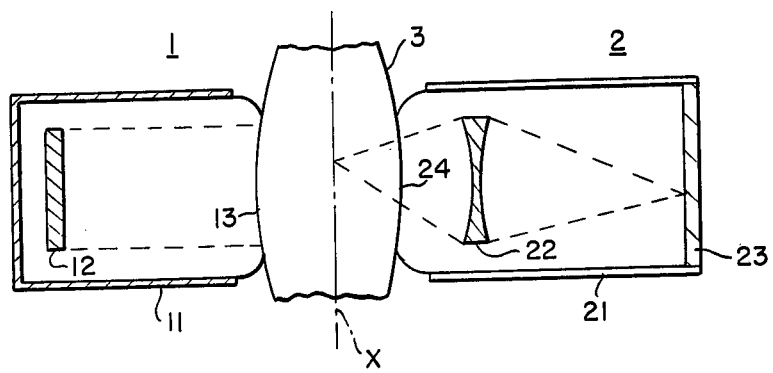
FIG. 1 illustrates the structure of the prior ultrasonic wave tomographic imaging system using a camera method on which this invention is based.
Figure 2:
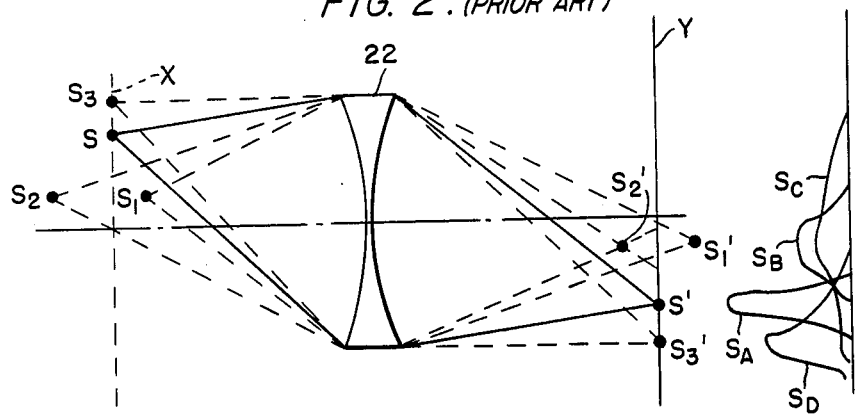
FIG. 2 explains the space noise of the prior ultrasonic wave tomographic imaging system illustrated in FIG. 1.
Figure 20:
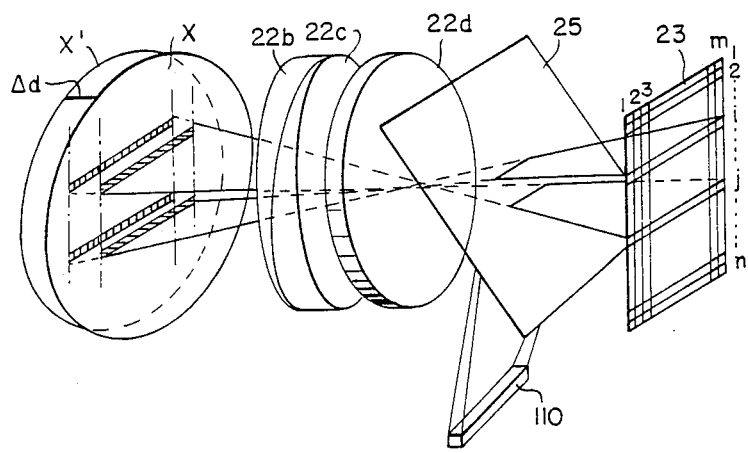
FIG. 20 and FIGS. 21(A) to (D) explain an embodiment of the tomographic plane changing technique used in this invention.

FIG. 20 explains the principle of this system. In this figure, 110 is the generator consisting of at least three lines of a piezoelectric conversion element matrix, and the ultrasonic wave can be focused on the line i, for example, by giving a phase difference to the drive signals applied to the center piezoelectric conversion element group and to the two lines of piezoelectric conversion element groups on both sides. It is also possible to move the straight focusing line along the tomographic plane X by changing said phase difference, but in the "Figure 20" it is moved along the plane X by means of the comb-shaped prisms 22b and 22c. For instance, it is moved to the straight line j. Namely, an electrical focusing method is realized. Application of this electrical focusing method to the column direction of the piezoelectric conversion element matrix makes possible a spot-by-spot scanning. In addition, 25 is is a half mirror, consisting of a polystyrene or acrylic material. 22b and 22c are the acoustic comb-shaped prisms which are rotated mechanically, thereby deflecting the ultrasonic wave generated from the generator 110 so that it is radiated to the specified location on the tomographic plane X. The generator 110, half mirror 25, comb-shaped prisms 22b and 22c are all housed in the case 21 as indicated in FIG. 1 as in the case of the lens 22 and transducer 23.

If there are regions having different acoustic impedance on the lines i and j of the surface X, the focused ultrasonic wave is reflected or scattered and transmitted in the direction vertical to the surface X. The transmitted wave is converged again by the ultrasonic wave lens 22d and then focused on the transducer 23 provided at the image forming surface Y.

Figure 17A:
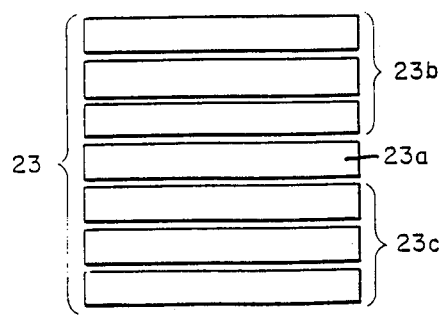
FIGS. 17(A) to (C) explain an embodiment of the selective reception technique used in the embodiment of FIG. 16.
Figure 17B:
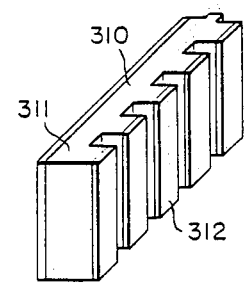
Figure 17C:
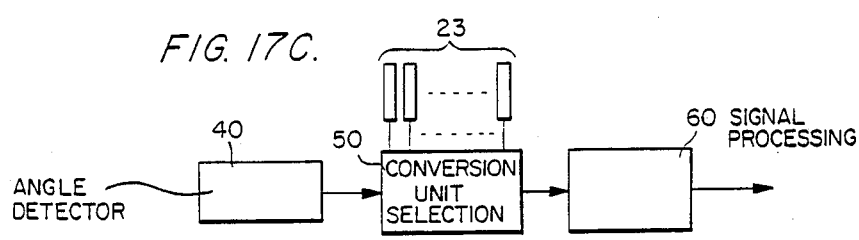

The transducer 23 is composed, for example, of the piezoelectric conversion elements arranged in the form of an m x n matrix, and the acoustic images of lines in the plane X are respectively focused on the piezoelectric conversion element groups the on the transducer 23 as in FIG. 19, the transducer operation for example being the same as that of FIGS. 17(A)-(C).

Therefore, an image corresponding only to the radiated region can be obtained by introducing such an electrical space gate means wherein if the line i is radiated, an output of the piezoelectric conversion element group of the i-th row is extracted at the time when the reflected wave reaches the transducer 23, while if the line j is radiated, an output of the piezoelectric conversion element group of the j-th row is extracted.

In addition, an image of the plane X' which is deeper than the plane X by a distance $\Delta d$ can also be obtained by a timing gate means which is delayed by a time $\Delta t$ required by the wave to be transmitted for the distance 2·$\Delta d$ from the plane X.

Thus, by changing the gate timing of this timing gate means, not only the plane X but also a plane which is shifted to the generator side by a distance $\Delta d$ or the plane X' which is deeper than the plane X can also be observed by means of the receiving signal of the receiver 23.

Figure 21A:
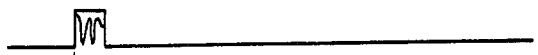
Figure 21B:
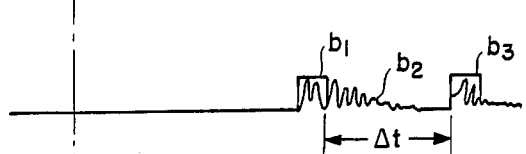
Figure 21C:
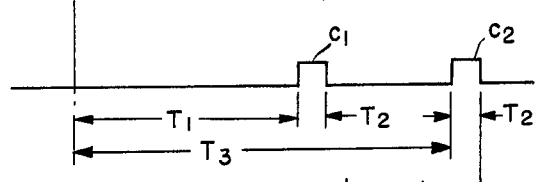
Figure 21D:

FIGS. 21(A) to (D) illustrate the transmitting and receiving waveforms. FIG. 21(A) is the generating waveform of the generator 110. FIG. 21(B) is the receiving wave form of the transducer 23 before it is gated electrically. FIG. 21(C) is the gate signal waveform and FIG. 21(D) is the gated receiving waveform. As indicated in FIG. 21 (B), the multiple reflected waves coming to the regionally radiated area are delayed in timing from the not-reflected wave. Namely, an acoustic output b2 of the multiply reflected wave is delayed as compared with an acoustic output b1 of the radiated wave.

For this reason, only the acoustic output b1 can be obtained by giving such a gate signal $C_1$ (FIG. 21 (C)) for attenuating an acoustic output b2. An ultrasonic image of the plane X' is received with a delay time of $\Delta t$.

Therefore, only an output b3 can be extracted by giving the gate signal $C_2$ after the time $T_3$.

The time $T_1$ from generation of the ultrasonic wave to gating can be determined by the location of the desired focusing point. In addition, the gating time $T_2$ can be determined by the number wave and their route differences in the acoustic optical system.

Figure 22:
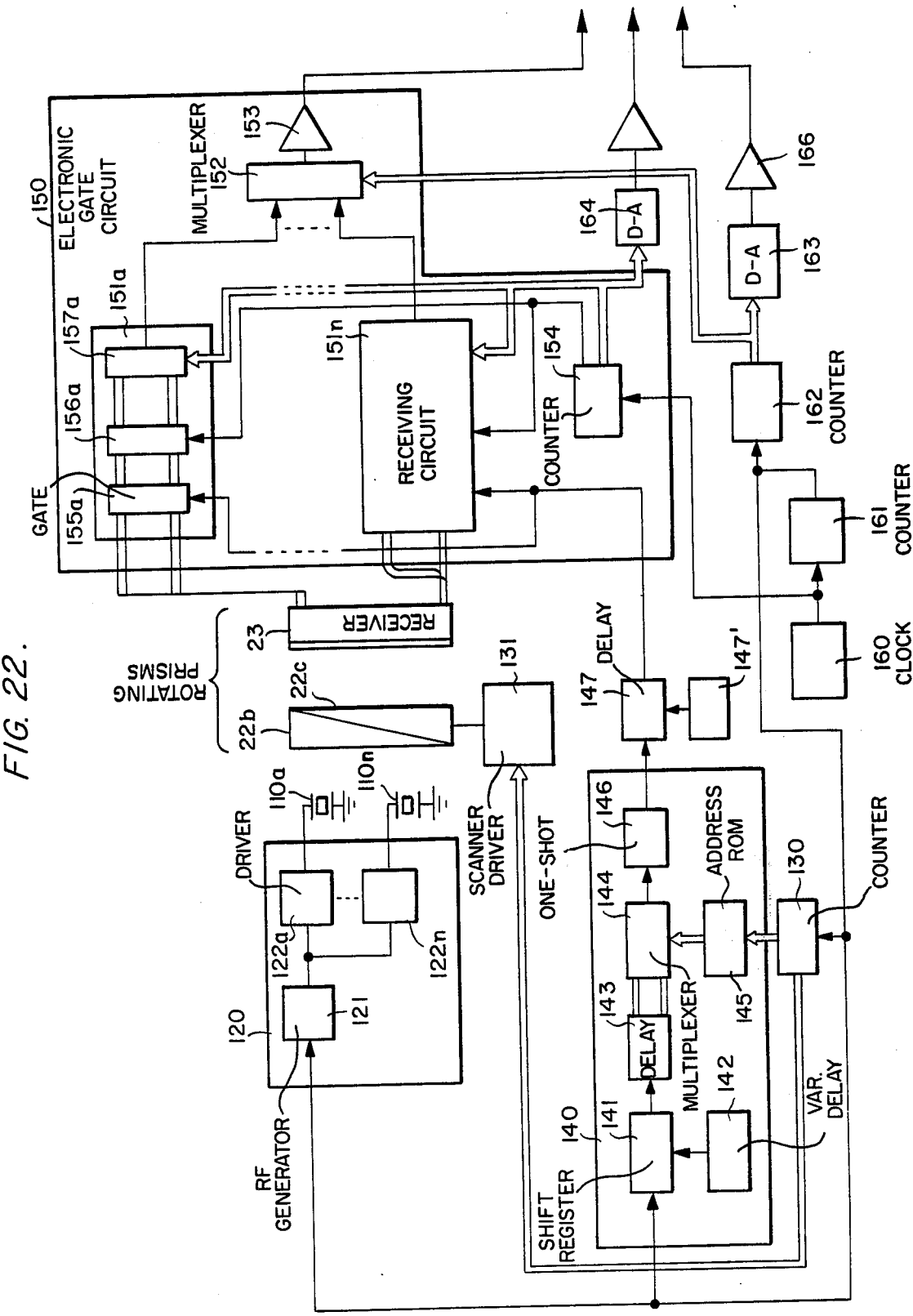
FIG. 22 indicates a block diagram of the embodiment of FIG. 20.

FIG. 22 illustrates the block diagram of an embodiment of the tomographic plane changing technique used in this invention.

In this figure, the same portions as those in FIG. 15 are given the same symbols. 120 is the transmitting drive circuit which drives in synchronization the piezoelectric conversion elements 110a to 110n of the generator 110 for transmitting the oscillated ultrasonic waves. 130 is the scanning position address counter, and 131 is the scanner driver which sequentially rotates the comb-shaped prisms 22b, 22c in accordance with a value of the address counter 130 for the scanning as indicated in FIG. 20. 140 is the gate signal generator. 150 is the electronic gate circuit which receives outputs of the piezoelectric conversion elements of each row and column of the piezoelectric conversion element array and samples an output of the piezoelectric conversion element of the specified row with the address signal and an output of the gate signal generator 140. 160 is the reference clock generator, 161 is the 256-bit counter for generating the horizontal synchronization signal, 162 is the horizontal synchronization signal address counter, 163 and 164 are the digital-analog converters, 165 and 166 are the amplifiers.

The transmitting drive circuit 120 is composed of the RF wave oscillator 121 and the drive circuits 122a to 122n for individually driving the piezoelectric conversion element groups 110a to 110n.

The RF wave generator 121 generates, when an output of the horizontal synchronization signal counter 161 is input thereto, a burst wave which is composed of a plurality of sine waves. Usually two to three RF waves are used.

An output of the RF wave generator 121 is input to the drive circuits 122a to 122n.

The drive circuits 122a to 122n operate as the amplifiers.

The address counter 130 counts the horizontal synchronization signal, which controls the scanner driver 131.

For example, when the number of scanning lines of display screen is selected to 256, The address counter 130 operates as a 256-bit counter. Namely, the address counter 130 generates addresses from 0 to 255 which become the location information of the prisms 22b and 22c.

On the other hand, the burst wave output of the RF wave generator is amplified by the amplifiers 122a to 122n, and is given to the piezoelectric conversion elements 110a to 110n. Thereby the piezoelectric conversion elements 110a to 110n are driven, generating ultrasonic waves.

Therefore, the tomographic plane is scanned sequentially while the electronic focusing operation is carried out during generation of the ultrasonic wave to the region corresponding to the address designated by the address counter 130 when the scanner driver 131 locates the scanner so that the ultrasonic wave is focused thereto.

In synchronization with the electronic scanning operation by the horizontal synchronization signal, the gate signal is also generated.

Namely, the gate signal generator 140 comprises the shift register 141, the variable time clock generator 142, delay circuit 143, multiplexer 144, address memory 145 consisting of a read-only-memory and gate width set-up circuit 146 consisting of a one-shot multivibrator.

The horizontal synchronization signal is delayed by the shift register 141, and a delay time can be controlled by an output of the variable time clock generator 142. A delay time of the shift register 141 is adjusted so that the ultrasonic wave generated from the generator 110 passes on object 3 and reaches the receiving element 23 through the lens with the minimum time.

A delay time of the horizontal synchronization signal delayed by the shift register 141 is fine-adjusted by the delay circuit 143. This delay time can be ajusted by compensating for a small difference of the incoming time in individual focusing and scanning in case the scanning lines are 256, for example.

Therefore, the delayed outputs corresponding to the number of the scanning lines, for example, 256 outputs are obtained from the delay circuit 143.

This output is input to the multiplexer 144. On the other hand, an address for focusing and scanning is given from the address counter 130. The address register 145 receives this address and outputs the selection signal to the multiplexer 144 in order to select the optimum delay output for scanning of this address.

An output of this multiplexer 144 is widened for the width as wide as the time corresponding to the number of RF waves by the gate width set-up circuit consisting of the oneshot multivibrator and generated as the gate signal. This gate signal is input to the variable delay circuit 147 and delayed by the abovementioned time $\Delta t$. The variable delay circuit 147 is connected, for example, with the tomographic plane setting circuit 147, By changing the setting of the setting circuit 147, the tomographic plane location can be set from a delay time.

Meanwhile, the electronic gate circuit 150 is connected with the piezoelectric conversion elements of the matrix 23 of n rows and m columns. The m output of the piezoelectric conversion elements in the first row are input to the receiving circuit 151a, etc. and the m outputs of the piezoelectric conversion elements in the n-th row are input to the receiving circuit 151n.

The receiving circuits 151a to 151n are composed of the gate circuits 155a to 155n, memory circuits 156a to 156n and multiplexer circuits 157a to 157n. The gate circuits 155a to 155n and memory circuits 156a to 156n each include m circuits, but in the figure they are indicated by only one block.

To the m gate units of the gate circuits 155a to 155n the abovementioned gate signals are input.

The gate circuits 155a to 155n output m receiving inputs obtained by the gate signal to the memory circuits 156a to 156n. The m memory units of the memory circuits 156a to 156n respectively store the gate outputs.

On the other hand, the address counter 154 of the electronic gate circuit 150 receives clock pulses of the reference clock generator 160, counts them and outputs a counted value. This address conter 154 actually includes a plurality of counters, in number equal to the number of columns of the piezoelectric conversion element matrix, and is designed as an m-bit counter.

The counted values that are output are input to the multiplexers 157a to 157n and therefore the parallel outputs of the multiplexers 157a to 157n are converted to the serial outputs. The memory circuits 156a to 156n are reset by a count-up signal of the address counter 154 for the next receiving input.

These n serial outputs are input in parallel to the multiplexer 152. On the other hand, the multiplexer 152 receives a counted value of the address counter 162 which counts the horizontal synchronization signals.

Therefore, the multiplexer 152 outputs only one serial input corresponding to a counted value of the address counter 162 among n serial inputs. The address counter 162 is designed as an n-bit counter, covering the n rows of the matrix. Therefore, when the number of scanning lines is selected to 256, n is selected to 256.

An output of this multiplexer 152 is amplified by the amplifier 153 and is used by the display unit as the luminance signal.

Meanwhile, an output of the address counter 162 is coverted to an analog signal by the digital-analog converter 163, amplified by the amplifier 166 and used as the vertical (Y-axis) deflection signal for the display unit. Similarly, an output of the address counter 154 is also converted to an analog signal by the digital-analog converter 164, amplified by the amplifier 165 and used as the horizontal (X-axis) deflection signal for the display unit.

The abovementioned operations are summarized below. The drive circuits 122a to 122n are controlled so that the ultrasonic waves are focused and scanned to the scanning position of the plane specified by the address counter 130, the gate signal which is delayed in accordance with the scanning position specified is generated by the gate signal generator 140, a delay time of this gate signal is changed by the variable delay circuit 147, each receiving input of the m x n piezoelectric conversion element matrix 23 is sampled by this changed gate signal, the sampled signal is then converted to the serial signal, and thereafter the serial signal corresponding to the row of the receiving position corresponding to said scanning position specified by the address counter 162 is output by the multiplexer circuit 152.

Then, another embodiment of the tomographic plane changing technique will be explained.

Figure 23:
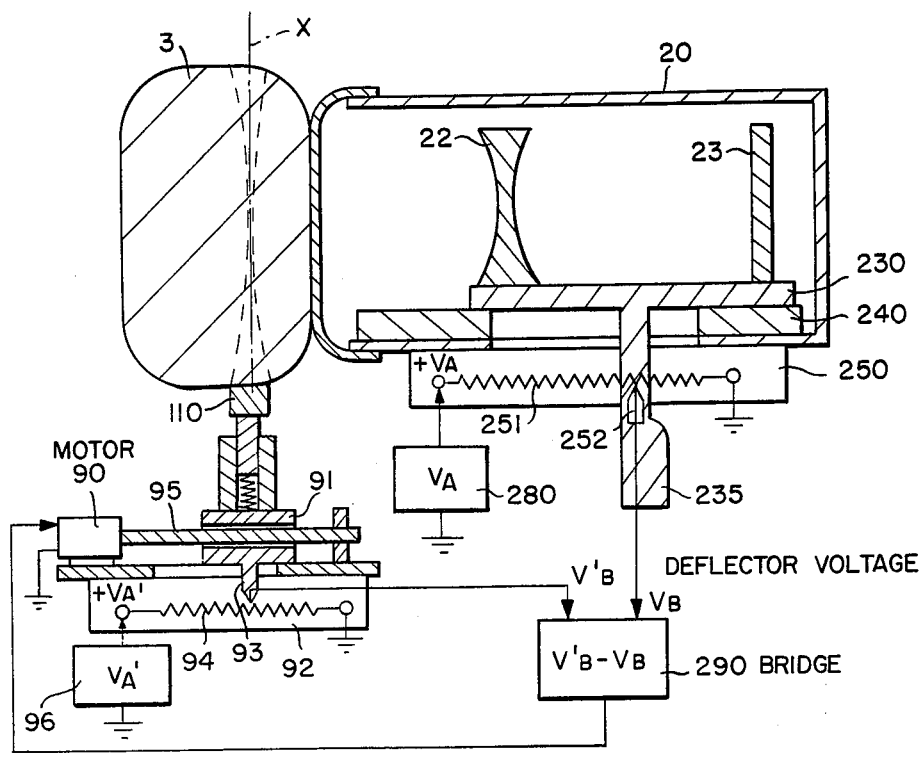
FIG. 23 explains another embodiment of the tomographic plane changing technique used in this invention.

FIG. 23 illustrates another embodiment of the tomographic plane changing technique used in this invention.

The ultrasonic transducer 110 which with an ultrasonic wave generating means is provided in contact with an object 3 in the vicinity of the plane X to be examined of the object 3. As a first means for moving the lens 22 and transducer 23 the movable bae 230 on which is mounted the lens 22 and transducer 23 is manually moved by the handle 235, the sliding base 240 which is in contact with the movable base 230 slides thereon, and the potentiometer 250 which detects the distance is moved by the movable base 230. As a second means for moving the ultrasonic wave transducer 110, the supporting base 91 supports the ultrasonic wave transducer, the screw rod 95 is engaged with the screwed hole of the supporting base 91, the DC motor rotates the screw rod 95 and the potentiometer 92 detects the location of supporting base 91.

A DC voltage $+V_A$ is supplied to the slide resistor 251 in the slidack 250 from a voltage regulator 280, while a DC voltage $+V_A'$ is supplied to the slide resistor 94 in the potentiometer 92 from a voltage regulator 96. A voltage $V_B$ detected by a sliding terminal 252 which operates in conjunction with the handle 235 and a voltage $V_B'$ detected by the sliding terminal 93 which operates in conjunction with the supporting base 91 are compared at the bridge circuit 290, and a voltage proportional to a difference $V_B'-V_B$ is supplied to a DC motor 90.

Here, it is supposed that the two sliding resistors 251 and 94 have the same resistance value and are homogeneous, and they are arranged in the same direction as indicated in the figure. When the values of $V_A$ and $V_A'$ are set equal and the movable base 230 is set to a certain location, the location of the supporting base 91 is determined so that $V_B$ and $V_B'$ become equal.

At this time, the second moving means as a whole is moved so that the ultrasonic wave transducer 1 is accurately located to the position of the plane X.

When the acoustic lens 22 and transducer 23 move together with the movable base 230 by means of the handle 135, a value of $V_B$ changes and a DC motor rotates until $V_B'$ becomes equal to $V_B$ and the ultrasonic transducer 110 moves together with the supporting base 91 for the same distance as mentioned above and in the same direction as the movable base 230. On the other hand, the distance b between the lens 22 and transducer 23 is maintained to a constant value during such movement and therefore the location of the tomographic plane X also moves in the same distance and in the same direction as the movable base 230. Therefore, the ultrasonic transducer 110 is moved accurately to the location of the plane X.

In above embodiment, the acoustic lens 22 and transducer 23 move together, but it is also possible for changing the location of the plane X to be examined to change the distance b between the acoustic lens 22 and transducer 23 by moving the acoustic lens 22 or transducer 23. In this case, as the method for responding to the second moving means, a moving distance of the lens or transducer is detected, a new value of b is calculated from the moving distance, a moving distance x of the plane X to be moved is obtained by calculating a distance between the plane X and the acoustic lens from said value of b and the focal distance of the acoustic lens, and the ultrasonic transducer is moved by the distance x.

These detecting means, calculation means and moving means are all easily realized by well known methods.

As explained previously, this invention assures noiseless and clear tomographic plane images by providing a means for generating ultrasonic wave in such a way as to scan the desired tomographic plane of an object and a gate means which allows the ultrasonic wave receiving means to receive an acoustic image corresponding to said scanning in accordance with the scanning by said ultrasonic wave generating means, and in addition, offers outstanding industrial advantages.

We claim:

1. An ultrasonic wave tomographic imaging system wherein an acoustic image of a desired tomographic plane in an object is focused on an ultrasonic wave receiving means by an ultrasonic wave lens, said system comprising
   generating means for generating focused ultrasonic waves from along a direction that is contained in a plane in space that includes said tomographic plane in said object, and for sequentially scanning said tomographic plane in said object with said focused ultrasonic waves, said direction being oriented essentially transversely to the axis of said lens, and
   a gate means for allowing said ultrasonic wave receiving means to selectively receive the ultrasonic waves of said acoustic image that are focused by said lens, in correspondence with said scanning of said tomograhic plane in said object by said generating means.

2. The system of claim 1, said generating means comprising further means for generating further focused ultrasonic waves from along the opposite direction in said plane containing said desired tomographic plane, for providing in unison said scanning of said tomographic plane.

3. The system of claim 1 or 2, comprising
   said generating means providing said scanning by focusing the generated ultrasonic waves effectively in sequential rows in said tomographic plane in said object,
   said receiving means comprising at least one respective conversion unit corresponding effectively to each said row in said tomographic plane, each said conversion unit of said receiving means comprising plural column elements for detecting the ultrasonic waves that are focused by said lens from respective column portions of the corresponding row in said tomographic plane, and
   said gate means including means for selectively activating said column elements of each said conversion unit of said receiving means in predetermined correspondence to said scanning of said focused ultrasonic waves in said tomographic plane, and for selectively gating in time the outputs of the plural column elements of each said conversion unit of the receiving mens to selectively detect respective portions of said ultrasonic waves of said acoustic image focused by said lens,
   wherein the ultrasonic waves received by said receiving means selectively originate from respective parts of said object in the vicinity of said tomographic plane at which said focusing by said generating means occurs.

4. The system of claim 3, said receiving means comprising
   said at least one conversion unit with said column elements located in the vicinity of said axis of said lens, and
   a deflector device for deflecting the ultrasonic waves focused by said lens onto said receiving means in correspondence with said scanning in the tomographic plane with said generating means.

5. The system of claim 3, said receiving means comprising a plurality of said conversion units, and means for selectively activating said conversion units in correspondence with said scanning.

6. The system of claim 3, said receiving means including a single one of said conversion units, said receiving means comprising a slit mechanism for moving reciprocally in front of the column elements in correspondence with said scanning in said tomographic plane.

7. An ultrasonic wave tomographic imaging system wherein ultrasonic waves from a desired tomographic plane in an object are focused on an ultrasonic wave receiving means by means of a ultrasonic wave lens, said system comprising
   generating means including at least one conversion unit for generating ultrasonic waves to be focused by said lens in said tomographic plane for sequentially scanning said tomographic plane in said object,
   gate means for allowing said ultrasonic wave receiving means to selectively receive the ultrasonic waves focused by said lens onto said receiving means in correspondence with said scanning of said tomographic plane,
   said receiving means comprising at least said at least one conversion unit of said generating means,
   a deflector device for deflecting said ultrasonic waves generated by said first conversion unit for providing said scanning in said tomographic plane of said object, and
   each said conversion unit comprising a plurality of column elements corresponding to respective column portions in said tomographic plane,
   wherein said gate means includes means for selectively selecting each conversion unit of said receiving means for selectively receiving said focused ultrasonic waves from said tomographic plane in correspondence to said scanning thereof, while compensating for the motion of said deflector device during the travel time of the generated waves until they are received by the receiving means.

8. The system of claim 7,
said receiving means including a single one of said conversion units,
said gate means comprising a mechanical slit apparatus aligned in parallel with the single conversion unit, and connected to move simultaneously across all of said column elements thereof in correspondence with said scanning of said tomographic plane,
wherein the motion of said slit allows all of said column elements to selectively generate said ultrasonic waves to be focused by said lens for providing said scanning selectively in said tomographic plane, and allows said selective reception by said receiving means in correspondence to the position of the slit at the time of receiving the selectively generated waves.

9. The system of claim 7, said receiving means comprising a plurality of said conversion units aligned in rows, and said gate means including a selector for selectively activating the column portions of at least one of said plural conversion units at a time, in conjunction with said deflecting of the deflector device, wherein at least one respective one of said conversion units selectively detects the ultrasonic waves being received by said receiving means.

10. The device of claim 7, 8 or 9, said gate means comprising means for selectively gating the detection of the ultrasonic waves received by each said conversion unit, so as to vary the position of said tomographic plane in said object along a direction parallel to the axis of said lens.

* * * * *

UNITED STATES PATENT AND TRADEMARK OFFICE
CERTIFICATE OF CORRECTION

PATENT NO. : 4,434,658
DATED : 6 March 1984
INVENTOR(S) : Miyazaki et al

It is certified that error appears in the above-identified patent and that said Letters Patent is hereby corrected as shown below:

Col. 1, line 10, delete "the" (second occurrence);
line 11, after "wave," insert --the--;
line 30, "of human" should be --of the human--;
line 38, after "basis" insert --,--;
line 48, "side" should be --sides--.

Figure 3A:
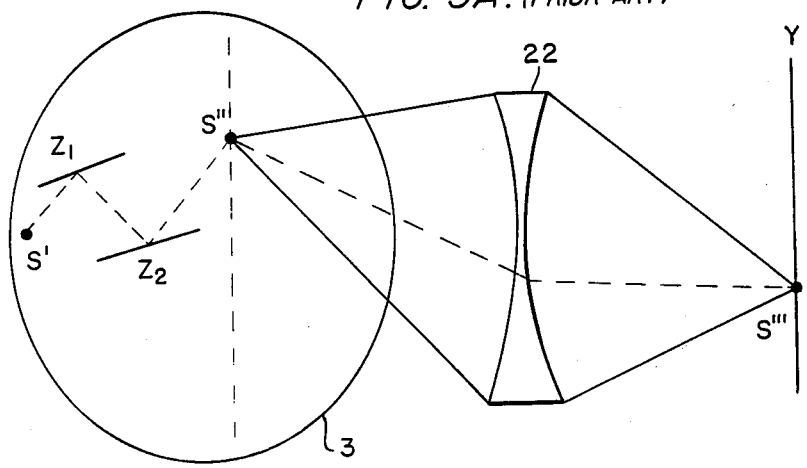
FIGS. 3(A) and (B) explain the timing noise of the prior ultrasonic wave tomographic imaging system in FIG. 1.
Figure 3B:
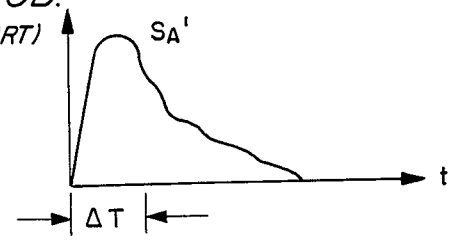

Col. 2, line 43, "a" should be --an--;
line 49, "a" should be --an--;
line 67, after "FIG. 3(B)," insert --forming--;
line 68, delete ",".

Col. 3, line 16, "a" should be --an--;
line 30, "ulrasonic" should be --ultrasonic--;
line 31, after "generating" insert --means--;
line 67, after "wave" insert --image--.

Col. 4, line 9, "operate" should be --operates--.

Col. 5, line 10, "line" should be --lines--;
line 19, "at" should be --of--.

Col. 7, lines 50-51, the small italic print should be the same as the rest of the text.

Col. 8, line 37, after "three" insert --sine--.

UNITED STATES PATENT AND TRADEMARK OFFICE
CERTIFICATE OF CORRECTION

PATENT NO. : 4,434,658

DATED : 6 March 1984

INVENTOR(S) : Miyazaki et al

It is certified that error appears in the above-identified patent and that said Letters Patent is hereby corrected as shown below:

Col. 11, line 7, delete "be";
line 23, delete "," (second occurrence).

Col. 12, line 34, "follow" should be --follows--.

Col. 14, line 36, after "be" insert --provided--.

Col. 15, line 14, delete "the" (first occurrence);
line 66, "110n" should be in dark print, as is "110a" on the same line.

Col. 16, line 23, "RF" should be --sine--;
line 24, after "used" insert --per burst--;
line 33, "The" should be --the--.

Col. 17, line 20, "By" should be --by--.

Col. 18, line 33, "bae" should be --base--.

Col. 19, line 12, after "In" insert --the--.

Col. 20, line 16, "mens" should be --means--;
line 45, "a" should be --an--.

Signed and Sealed this

Twelfth Day of February 1985

[SEAL]

Attest:

DONALD J. QUIGG

Attesting Officer

Acting Commissioner of Patents and Trademarks